US008227239B2

(12) United States Patent
Busujima et al.

(10) Patent No.: US 8,227,239 B2

(45) Date of Patent: Jul. 24, 2012

(54) CULTURE APPARATUS

(75) Inventors: Hiroki Busujima, Ota (JP); Yasuhiro Kikuchi, Ota (JP); Kenichi Ito, Oizumi-machi (JP); Kuniyoshi Kobayashi, Oizumi-machi (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 177 days.

(21) Appl. No.: 12/703,532

(22) Filed: Feb. 10, 2010

(65) Prior Publication Data

US 2010/0167383 A1 Jul. 1, 2010

Related U.S. Application Data

(63) Continuation of application No. PCT/JP2009/064525, filed on Aug. 19, 2009.

(30) Foreign Application Priority Data

Aug. 26, 2008 (JP) ................................ 2008-216756
Sep. 3, 2008 (JP) ................................ 2008-225410

(51) Int. Cl.
*C12M 1/36* (2006.01)
*A61L 2/10* (2006.01)

(52) U.S. Cl. .................. 435/286.1; 435/303.1; 435/809; 422/24; 250/455.11

(58) Field of Classification Search ............... 435/303.1, 435/809, 286.1; 422/24; 250/455.11
See application file for complete search history.

(56) References Cited

U.S. PATENT DOCUMENTS 4,475,900 A * 10/1984 Popovich et al. ............... 604/28
6,255,103 B1 * 7/2001 Tamaoki et al. ........... 435/303.1
2008/0112844 A1 * 5/2008 Garrett ............................. 422/4

FOREIGN PATENT DOCUMENTS

JP 2000-166536 A 6/2000

OTHER PUBLICATIONS

English langauge version of PCT/IB/373 of PCT/JP2009/064525 (Apr. 12, 2011).*
"Regarding Method of Aseptic Sterilization by Ray Sterilizing Lamp", Furumi Hiroshi, vol. 25, No. 9, pp. 14-23, 1983.
International Search Report for PCT/JP2009/064525 mailed Sep. 15, 2009 and Written Opinion of ISA for PCT/JP2009/064525 mailed Sep. 15, 2009 (9 pages).

* cited by examiner

*Primary Examiner* — William H Beisner
(74) *Attorney, Agent, or Firm* — Osha Liang LLP

(57) ABSTRACT

A culture apparatus comprising: a housing including a culture chamber inside, culture being cultured in the culture chamber; a door configured to seal the culture chamber; an ultraviolet lamp configured to generate an ultraviolet ray for disinfecting air in the culture chamber; a lighting device configured to allow the ultraviolet lamp to be on for a predetermined time period, when the air in the culture chamber is disinfected; a detecting device configured to detect deterioration of disinfection capability of the ultraviolet lamp; and a controller configured to correct the predetermined time period, during which the ultraviolet lamp is on, so as to be longer according to the deterioration of the disinfection capability of the ultraviolet lamp detected by the detecting device.

3 Claims, 6 Drawing Sheets

START
S100 IS OUTER DOOR CHANGED FROM CLOSED TO OPEN? NO / YES
S101 IS OUTER DOOR CHANGED FROM OPEN TO CLOSED? NO / YES
S102 RESET TIMER AND START TIMING
S103 TURN ON RELAY
S104 READ OUT ACCUMULATED LIGHTING TIME (t2) OF ULTRAVIOLET LAMP FROM RAM
S105 OBTAIN t1 FROM t2 REFERRING TO TABLE DATA
S106 t=t1 ? NO / YES
S107 TURN OFF RELAY
S108 t2=t2+t1
S109 STORE t2 IN RAM
S110 t2≧t3? NO / YES
S111 NOTIFY THAT LAMP IS JUST ABOUT DEAD
S112 IS OUTER DOOR CHANGED FROM CLOSED TO OPEN? NO / YES
S113 TURN OFF RELAY
S114 t2=t2+t
S115 STORE t2 IN RAM

CULTURE APPARATUS

CROSS-REFERENCE TO RELATED APPLICATIONS

This is a continuation application of International Patent Application No. PCT/JP2009/064525 filed Aug. 19, 2009, which claims the benefit of priority to Japanese Patent Application Nos. 2008-216756 and 2008-225410, filed Aug. 26, 2008 and Sep. 3, 2008, respectively. The full contents of the International Patent Application are incorporated herein by reference.

BACKGROUND OF THE INVENTION

1. Field of the Invention

The present invention relates to a culture apparatus.

2. Description of the Related Art

There is known a culture apparatus that cultures culture such as a cell, a microorganism and the like in a culture chamber. This type of culture apparatus includes a housing in which the culture chamber is formed, a door for sealing the culture chamber, and an ultraviolet lamp that generates an ultraviolet ray for disinfecting air in the culture chamber, and it is configured such that when detecting sealing of the culture chamber with the door, the ultraviolet lamp is on for a predetermined time period.

The ultraviolet lamp disinfects water for humidification in a humidification tray located on a bottom face of the culture chamber, for example, and as a means for detecting sealing of the culture chamber with the door, a micro switch or the like is used which is configured such that the switch is in an OFF state when the door is open, while the switch is in an ON state when the door is closed.

An operation of sealing the culture chamber with the door is performed after a user opens the door to take out culture from the culture chamber or after the user places the culture in the culture chamber, for example, and at each time the operation is performed, the ultraviolet lamp is on for a predetermined time period. As a result, the air, water for humidification and the like in the culture chamber are disinfected, which are contaminated by bacteria in the atmosphere since the culture chamber is opened.

Irradiation time of the ultraviolet ray from the ultraviolet lamp for disinfecting bacteria is experimentally obtained in advance, and the predetermined time period during which the ultraviolet lamp is on at each lighting is set on the basis of this experiment results, for example (See Japanese Patent Laid-Open Publication No. 2000-166536).

In the culture apparatus including the above-mentioned configuration, as the operation of opening/closing the door of the culture chamber is repeated, an irradiation output of the ultraviolet lamp is lowered due to the repetition of irradiation of the ultraviolet lamp. That is, since the irradiation output of the ultraviolet lamp is gradually lowered according to lighting time period (aging characteristics), a disinfection effect of the ultraviolet ray (that is, disinfection capability of the ultraviolet lamp) generated by the ultraviolet lamp per predetermined time period is also lowered according to the lighting time period of the ultraviolet lamp.

Thus, the more time the lamp is used, the more insufficient the disinfection in the culture chamber performed by the ultraviolet ray from the ultraviolet lamp becomes. That is, there is lowered the disinfection effect of the ultraviolet lamp accompanied by the culture chamber being sealed with the door. In this case, there is a risk that the bacteria remaining in the culture chamber without being disinfected might grow and contaminate the culture.

SUMMARY OF THE INVENTION

A culture apparatus according to an aspect of the present invention, comprises: a housing including a culture chamber inside, culture being cultured in the culture chamber; a door configured to seal the culture chamber; an ultraviolet lamp configured to generate an ultraviolet ray for disinfecting air in the culture chamber; a lighting device configured to allow the ultraviolet lamp to be on for a predetermined time period, when the air in the culture chamber is disinfected; a detecting device configured to detect deterioration of disinfection capability of the ultraviolet lamp; and a controller configured to correct the predetermined time period, during which the ultraviolet lamp is on, so as to be longer according to the deterioration of the disinfection capability of the ultraviolet lamp detected by the detecting device.

The present invention has an object to compensate for deterioration of a disinfection effect of an ultraviolet lamp as lighting time period of the ultraviolet lamp is increased.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE INVENTION

At least the following details will become apparent from descriptions of this specification and of the accompanying drawings.

First Embodiment

Configuration of Culture Apparatus

Figure 1:
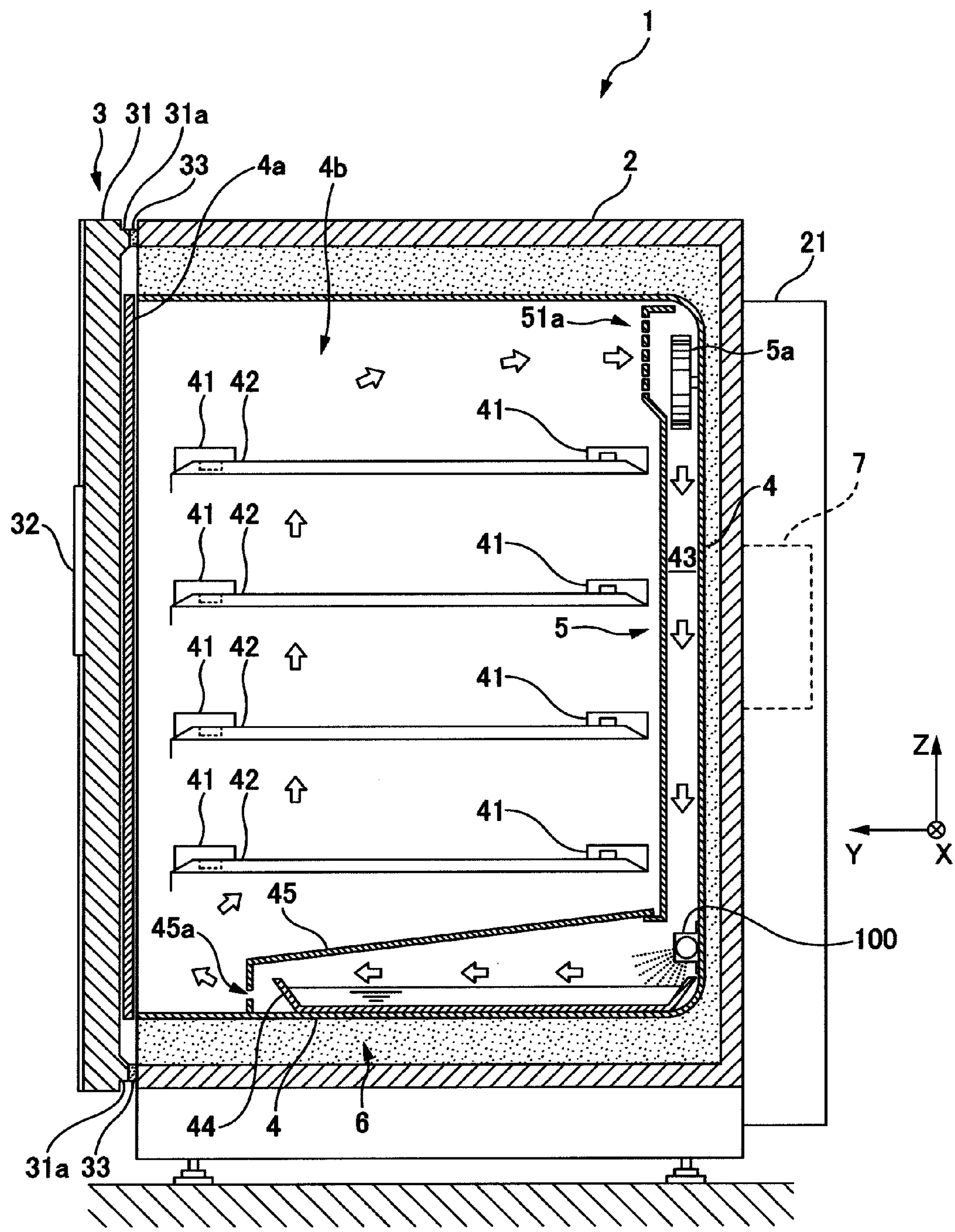
FIG. 1 is a side sectional view of an example of a culture apparatus according to a first embodiment.
Figure 2:
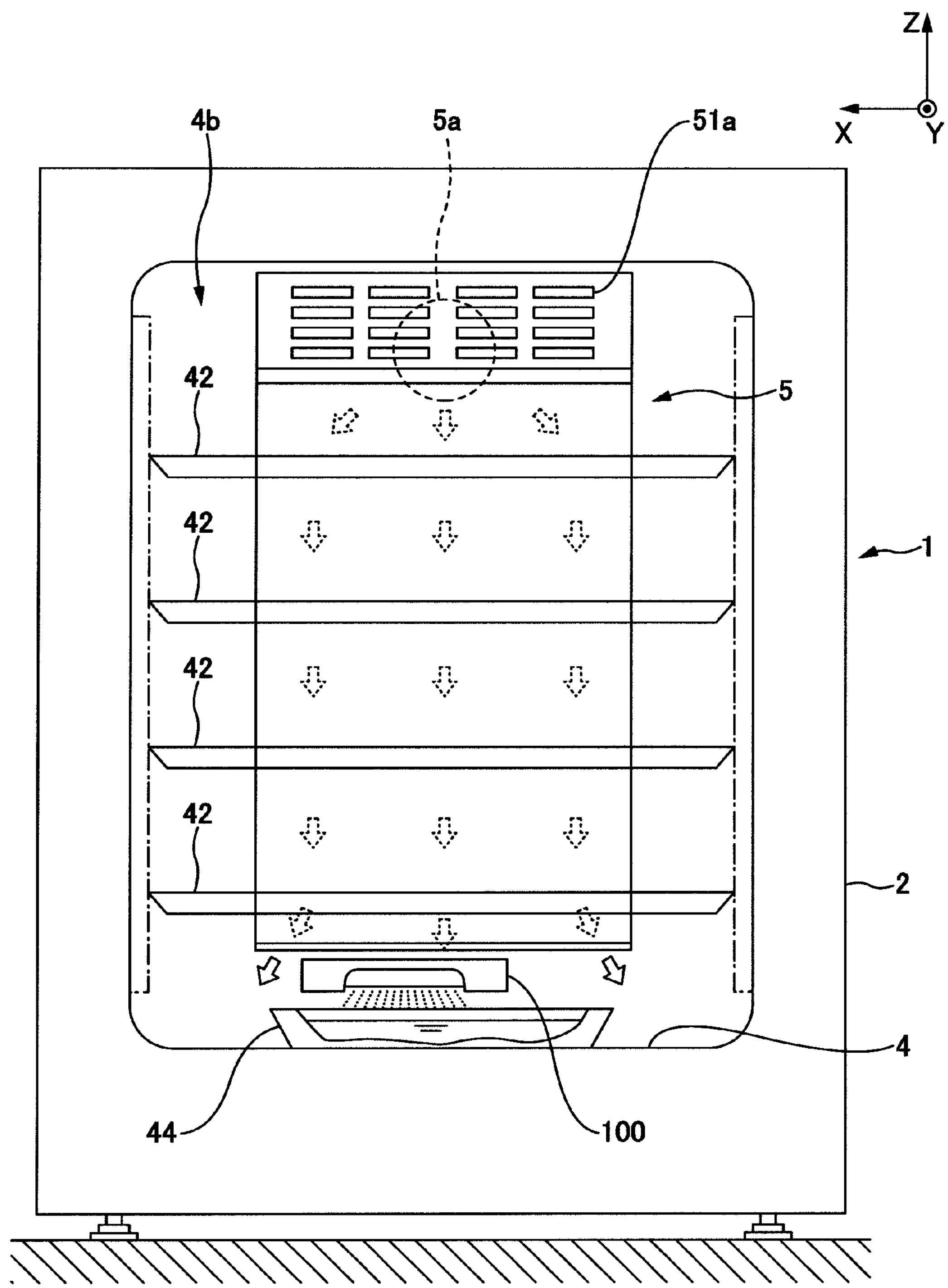
FIG. 2 is a front view of a culture apparatus in FIG. 1.
Figure 3:
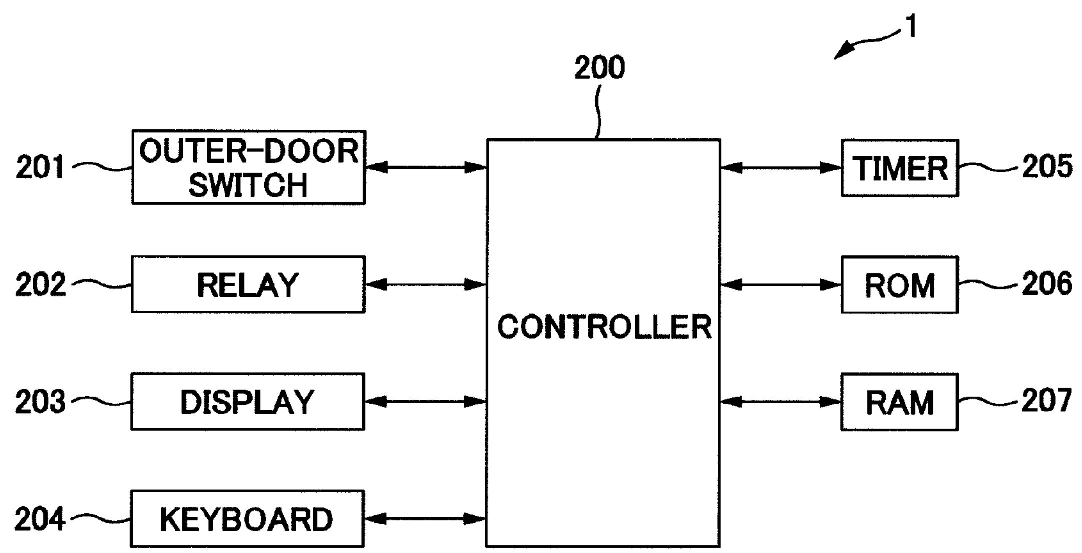
FIG. 3 is a block diagram illustrating an example of a configuration for controlling an ultraviolet lamp in a culture apparatus in FIG. 1.

Referring to FIGS. 1 to 3, a configuration example of a culture apparatus 1 according to a first embodiment will be described. FIG. 1 is a side sectional view of an example of the culture apparatus 1 according to a first embodiment. FIG. 2 is a front view of the culture apparatus 1 in FIG. 1. FIG. 3 is a block diagram illustrating an example of a configuration for controlling an ultraviolet lamp 100 in the culture apparatus 1 in FIG. 1. In FIG. 2, an outer door 3 and an inner door 4*a*, which will be described later, are omitted for convenience of illustration.

As exemplified in FIGS. 1 and 2, the culture apparatus 1 includes an inner box (housing) 4 and an outer box (housing) 2, the inner door (door) 4*a* and the outer door (door) 3, and the ultraviolet lamp 100. The culture apparatus 1 cultures a culture such as a cell, a microorganism in a culture chamber 4*b* of the inner box 4.

The inner box 4 is a substantially rectangular box made of stainless steel, for example, and the culture chamber 4*b* is formed inside the box. The culture chamber 4*b* exemplified in the figures is divided in the vertical direction (Z-axis direction) by a plurality of shelves 42 made of stainless steel, for example, on which the culture is to be placed. The shelf 42 has a plurality of through holes (not shown) formed by penetrating shelf in the vertical direction and is supported by shelf supports 41 in pairs made of stainless steel, for example, provided on an inner face of the inner box 4 on a ±X side.

The outer box 2 is a box made of stainless steel, for example, and having a substantially similar shape to that of the inner box 4 and houses the inner box 4 therein in a state insulated from the outside air. On an inner face of the outer box 2, an insulating material (not shown) for heat retention is provided, and an air jacket 6 is formed between the insulating material and the inner box 4, as a circulation path for air, for example, for further heat retention. On the air jacket 6, a heater (not shown) for adjusting a temperature inside the culture chamber 4*b* is mounted. Also, on an outer face on the rear side (−Y side) of the outer box 2, a sensor box 7 is provided which includes a sensor (not shown) for detecting a temperature inside the culture chamber 4*b*, a nozzle (not shown) for injecting a gas such as carbon dioxide into the culture chamber 4*b*, a sensor (not sown) for detecting a concentration of carbon dioxide in the culture chamber 4*b*, a heater (not shown) and the like, for example. The nozzle, the sensor and the like are mounted from outside the outer box 2 through a hole (not shown) drilled from the outer face on the rear side of the outer box 2 to the inner face on the rear side of the inner box 4, for example, and particularly the sensor or the like is electrically connected to a control unit 200, which will be described later, through a predetermined wiring (not shown), for example. The outer face on the rear side of the outer box 2 and the sensor box 7 are covered by a cover 21 including an insulating material (not shown) inside.

The inner door 4*a* is a flat-plate shaped door made of tempered glass, for example, which can open/close an opening on the front side (+Y side) of the inner box 4 through a predetermined hinge (not shown). When the inner door 4*a* is closed through predetermined packing (not shown) with respect to the opening of the inner box 4, the inside of the inner box 4 is made air tight against the outside.

The outer door 3 is a flat-plate shaped door made of metal, for example, which can open/close an opening on the front side of the outer box 2 through a predetermined hinge (not shown).

The outer door 3 includes a door main body 31 made of metal provided inside with an insulating material (not shown) for heat retention, a heater (not shown) for adjusting a temperature inside the culture chamber 4*b* and the like, and a packing 33 mounted on a projection portion 31*a* opposing the opening of the outer box 2 in the door main body 31. The outer door 3 further includes a control panel 32 on the front side of the door main body 31. This control panel 32 includes a keyboard 204 for setting lighting time period of the ultraviolet lamp 100, or the like, which will be described later, a display 203 for displaying their current values, and the like.

As exemplified in FIGS. 1 and 2, the ultraviolet lamp 100 is disposed at a position, at which an ultraviolet ray can be applied to air passing through a bottom of (−Z side) a duct 43 and to water for humidification in a humidification tray 44 arranged at the bottom of the duct 43 so as to disinfect bacteria in the air and water. Here, the duct 43 is made up of a wall on the rear side of the inner box 4 and a wall plate 5 made of stainless steel, between which an air passage is formed. At an upper part of the duct 43 (+Z side), a fan 5*a* (sirocco fan) is provided.

As exemplified in FIG. 1, the above-mentioned humidification tray 44 is entirely covered by a stainless cover 45, for example, having a hole 45*a* on the front side. Here, in FIG. 2, the cover 45 is omitted for convenience of illustration.

Also, as exemplified by open arrows in FIGS. 1 and 2, air on the shelf 42 side in an upper part of the culture chamber 4*b* flows into the duct 43 through an intake 51*a*, flows from the upper part to the bottom in the duct 43, and then, flows to the front on the water surface of the water for humidification, and humidified air goes through the hole 45*a* of the cover 45 and forms an ascending air current surrounding the plurality of shelves 42 by means of rotation of the fan 5*a* in one direction. The air having risen to the upper part of the culture chamber 4*b* flows into the duct 43 again through the intake 51*a*. By means of such circulation of air, the inside of the culture chamber 4*b* is maintained at substantially uniform temperature, humidity, and gas concentration such as carbon dioxide.

The ultraviolet lamp 100 is controlled so as not to generate an ultraviolet ray with a wavelength of 200 nm or less by an optical filter or the like. As a result, generation of ozone ($O_3$) from a gas (air, gas such as carbon dioxide, steam and the like) in the duct 43, for example, is also controlled. As a result, a bad influence of ozone on the culture in the culture chamber 4*b* is suppressed.

As exemplified in FIG. 3, the culture apparatus 1 is further includes the control unit 200, an outer-door switch 201, a relay 202, a timer 205, a ROM 206, and a RAM 207.

The control unit 200 includes a CPU (not shown) and controls the outer-door switch 201, the relay 202, the timer 205, the ROM 206, and the RAM 207 in a centralized manner. The display 203 and the keyboard 204 included in the above-mentioned control panel 32 are also controlled by the control unit 200.

The outer-door switch 201 is a micro switch provided in vicinity of the opening in the outer box 2, for example, and is made up so that the switch is in the ON state when a user closes the outer door 3 and in the OFF state when the user opens the outer door 3 with respect to the opening of the outer box 2.

The relay 202 supplies or shuts off power to the ultraviolet lamp 100 from a predetermined power source (not shown) by bringing a relay switch (not shown) into the ON state or the OFF state in response to a signal from the control unit 200. In an embodiment of the present invention, to turn on the relay switch so as to supply power to the ultraviolet lamp 100 is referred to as "to turn on the relay 202", while to turn off the relay switch so as to shut off power supply to the ultraviolet lamp 100 is referred to as "to turn off the relay 202".

The timer 205 measures lighting time period of the ultraviolet lamp 100, that is, a time period during which the relay 202 is on.

The ROM 206 stores a program or the like for executing control of the lighting time period of the ultraviolet lamp 100, which will be described later, for the control unit 200.

The RAM 207 stores data or the like used for controlling the lighting time period of the ultraviolet lamp 100, which will be described later. Specifically, this RAM 207 stores data indicating initial lighting time to, which is an initial value of the lighting time period of each lighting of the ultraviolet lamp 100, data indicating lighting time t1 obtained by adding a predetermined value to the initial value, and data indicating accumulated lighting time t2 of the ultraviolet lamp 100, which will be described later.

<Operation of Culture Apparatus>

Figure 4:
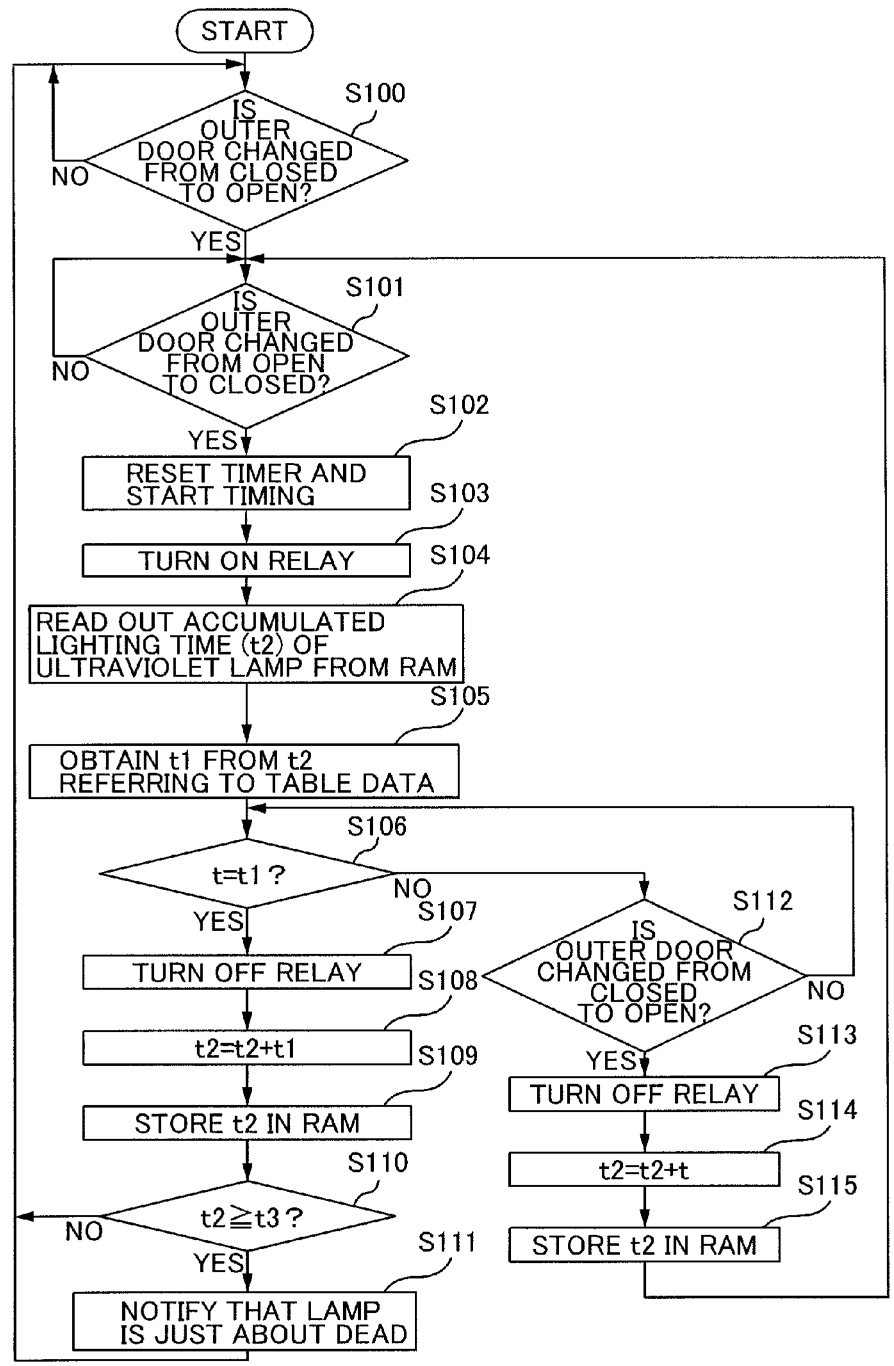
FIG. 4 is a flowchart illustrating an example of a processing procedure of a control unit in controlling lighting time period of an ultraviolet lamp according to a first embodiment.
Figure 5:
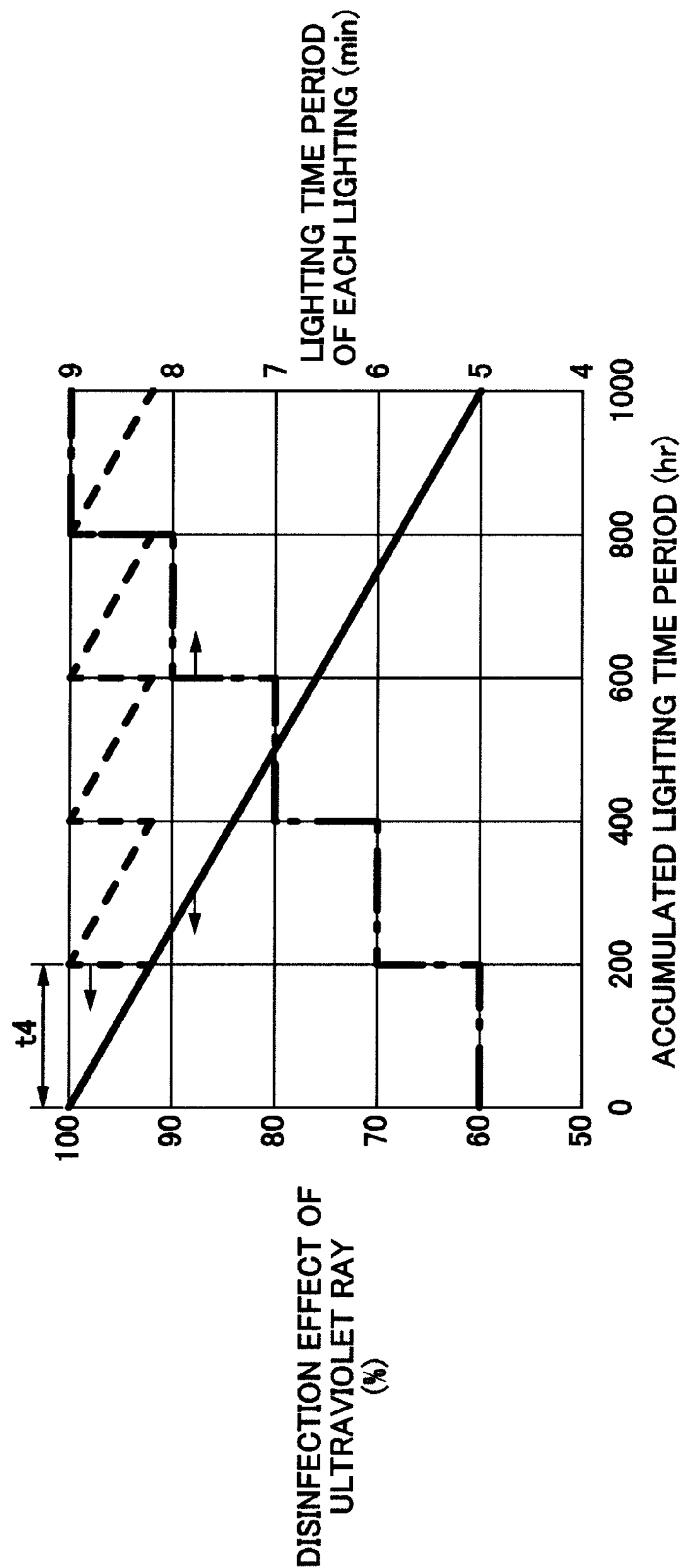
FIG. 5 is a diagram illustrating a relationship among a disinfection effect of an ultraviolet ray, accumulated lighting time period of an ultraviolet lamp, and a lighting time period at each lighting, according to a first embodiment.

Referring to FIGS. 4 and 5, an operation example of the culture apparatus 1 provided with the above-mentioned configuration will be described. FIG. 4 is a flowchart illustrating an example of a processing procedure of the control unit 200 in controlling lighting time period of the ultraviolet lamp 100 according to an embodiment of the present invention. FIG. 5 is a diagram illustrating a relationship among a disinfection effect of an ultraviolet ray, the accumulated lighting time period of the ultraviolet lamp 100, and the lighting time period at each lighting according to an embodiment.

As exemplified in FIG. 4, the control unit 200 determines whether the outer door 3 has been changed from a closed state to an open state (S100). Specifically, the control unit 200 determines if the outer-door switch 201 has been changed from the ON state to the OFF state.

If it is determined that the outer door 3 has been changed from the closed state to the open state (S100: YES), the control unit 200 then determines if the outer door 3 has been changed from the open state to the closed state this time (S101). Specifically, the control unit 200 determines if the outer-door switch 201 has been changed from the OFF state to the ON state. If it is determined that the outer door 3 has not been changed from the closed state to the open state (S100: NO), the control unit 200 executes processing of Step S100 again.

If it is determined that the outer door 3 has been changed from the open state to the closed state (S101: YES), the control unit 200 resets the timer 205 so as to start time-measuring (S102), turns on the relay 202 so as to turn on the ultraviolet lamp 100 (S103), reads out the accumulated lighting time t2 (accumulated time period) from the RAM 104 (S104), and obtains the lighting time t1 (predetermined time period) on the basis of the accumulated lighting time t2 (S105). In an embodiment of the present invention, the lighting time t1 of the ultraviolet lamp 100 is set at a time, which is set longer relative to the initial lighting time t0 (for example, 5 minutes, predetermined time period) by a predetermined value (1 minute, for example) every time the accumulated lighting time t2 has reached 200 hours, for example. Here, the lighting time t1 relative to the accumulated lighting time t2 is stored as table data (not shown) in the RAM 207, for example. If it is determined that the outer door 3 has not been changed from the open state to the closed state (S101: NO), the control unit 200 executes the processing of Step S101 again.

The above-mentioned table data is generated in the control unit 200 in advance on the basis of data input by a user through the keyboard 204 of the control panel 32 (the initial lighting time to, a length of one section t4 of the accumulated lighting time t2, a predetermined value (1 minute, for example) to be added to t0, and the like). For example, the higher the concentration of the bacteria is in an installation environment of the culture apparatus 1, the longer the initial lighting time t0 and the predetermined value (1 minute, for example) are preferably set. Also, the above-mentioned accumulated lighting time t2 is reset by the user to 0 through the keyboard 204 of the above-mentioned control panel 32 at a time when the ultraviolet lamp 100 is replaced with a new one, for example.

That is, when such a series of operations that the outer door 3 is opened and then closed are performed, the control unit 200 turns on the ultraviolet lamp 100 immediately after a closing operation, and each time the accumulated lighting time t2 has passed the predetermined section t4 (a predetermined time period, 200 hours, for example), the lighting time t1 is set longer by a predetermined value (1 minute, for example).

The control unit 200 refers to the timer 205 and determines whether or not a time t, which is measured by the timer, has reached the lighting time t1 which is obtained at Step S105 (S106).

If it is determined that the time t of the timer 205 has reached the lighting time t1 (S106: YES), the control unit 200 turns off the relay 202 (S107), obtains a new accumulated lighting time t2 by adding the lighting time t1, which is obtained at Step S105, to the accumulated lighting time t2, which is read out at Step S104 (S108), and updates the data in the RAM 206 with this new accumulated lighting time t2 (S109).

The control unit 200 determines whether or not the new accumulated lighting time t2, which is obtained at Step S108, has reached an accumulated lighting time t3 of the ultraviolet lamp 100, which is determined in advance (S110). If it is determined that this new accumulated lighting time t2 has reached the accumulated lighting time t3 (S110: YES), the control unit 200 notifies the user that the ultraviolet lamp 100 is just about dead through the display 203 or the like, for example (S111), as well as executes the processing of Step S100 again. On the other hand, if it is determined that the new accumulated lighting time t2 has not reached the accumulated lighting time t3 (S110: NO), the control unit 200 executes the processing of Step S100 again.

At the above-mentioned Step S106, if it is determined that the time t of the timer 205 has not reached the lighting time t1 (S106: NO), the control unit 200 determined whether or not the outer door 3 has changed from the closed state to the open state (S112). If it is determined that the outer door 3 has not changed from the closed state to the open state (S112: NO), the control unit 200 executes the processing of Step S106 again.

If it is determined that the outer door 3 has changed from the closed state to the open state (S112: YES), the control unit 200 turns off the relay 202, obtains the new accumulated lighting time t2 by adding the time t, which is timed by the timer at the time of Step S106, to the accumulated lighting time t2, which is read out at Step S104 (S114), updates the data in the RAM 206 with the new accumulated lighting time t2 (S115), and executes the processing of Step S101 again.

That is, the control unit 200 allows the ultraviolet lamp 100 to be on for the lighting time t1, which is determined according to the accumulated lighting time t2 each time such series of operations that the outer door 3 is opened and then closed are performed. However, if the outer door 3 is opened during this lighting time t1, the lighting time t till that point of time is added to the accumulated lighting time t2, and after the outer door 3 is closed again, the ultraviolet lamp 100 is allowed to be on for the lighting time t1, which is determined according to the new accumulated lighting time t2.

In the exemplification in FIG. 5, the disinfection effect of the ultraviolet ray of the ultraviolet lamp 100 is lowered with a linear relationship with the accumulated lighting time period. Specifically, the disinfection effect of the ultraviolet ray when the accumulated lighting time period is 0 hours is 100%, the disinfection effect is lowered linearly to 60% in 1000 hours (a solid line in FIG. 5).

Here, the disinfection capability of the ultraviolet lamp 100 is in proportion with an irradiation output of the ultraviolet lamp 100 per predetermined time period (5 minutes, for example). The longer the accumulated lighting time t2 becomes, the more the irradiation output of the ultraviolet lamp 100 is deteriorated, and thus, with deterioration the disinfection capability of the ultraviolet lamp 100 is lowered. On the other hand, the disinfection effect of the ultraviolet ray is in proportion with a product of the irradiation output of the ultraviolet lamp 100 and its lighting time period.

As exemplified by an alternate long and short dashed line in a stepped state in FIG. 5, by means of the above-mentioned processing of the control unit 200, the lighting time period of each lighting is set to 5 minutes (initial lighting time period) when the accumulated lighting time period is from 0 to 200 hours, the lighting time period of each lighting is set to 6 minutes when the accumulated lighting time period is from 200 to 400 hours, the lighting time period of each lighting is set to 7 minutes when the accumulated lighting time period is from 400 to 600 hours, the lighting time period of each lighting is set to 8 minutes when the accumulated lighting time period is from 600 to 800, and the lighting time period of each lighting is set to 9 minutes when the accumulated lighting time period is from 800 to 1000 hours.

That is, the lighting time period of each lighting of the ultraviolet lamp 100 is set so that an average gradient in a stepped state shown by the alternate long and short dashed line in FIG. 5 is substantially coincided in absolute value with a straight gradient shown by a solid line in the same figure. In this way, using a simple configuration of the timer 205 or the like, the lighting time t1 can be set on the basis of the relationship between the accumulated lighting time t2 of the ultraviolet lamp 100 and its disinfection capability.

As configured above, by extending the lighting time period of each lighting so as to compensate for the deterioration in the disinfection capability, which is lowered with a predetermined gradient relative to the accumulated lighting time period, as shown by a serrated dotted line in FIG. 5, for example, the disinfection effect of the ultraviolet lamp 100 can be maintained so as to have desired capability or better. As a result, the deterioration of the disinfection effect of the ultraviolet lamp 100 when the culture chamber 4*b* is sealed can be suppressed, and thus, contamination of culture by bacteria or the like intruding into the culture chamber 4*b* can be suppressed.

The shorter than 200 hours exemplified in FIG. 5 one section t4 for extending the lighting time period at each lighting is set, the smaller the deterioration in the disinfection effect of the ultraviolet ray per section t4 exemplified by the dotted line in the same figure is made, and thus, the contamination of the culture by the bacteria or the like intruding into the culture chamber 4*b* can be effectively suppressed. Here, the section t4 is stored as data in advance in the RAM 207. This section t4 can be changed in setting by the user through the keyboard 204 of the above-mentioned control panel 32. In this way, a predetermined time period during which the ultraviolet lamp 100 is on is set longer in a stepped manner for each section t4 of the accumulated lighting time period, to be able to effectively compensate for the deteriorated portion of the disinfection capability of the ultraviolet lamp 100.

Also, at the above-mentioned Step S105, in order to acquire the lighting time t1 corresponding to the accumulated lighting time t2, the table data stored in the RAM 207 is used, but it is not limitative. For example, the lighting time t1 may be calculated on the basis of the initial lighting time t0, the accumulated lighting time t2 as well as its section t4, and the predetermined value (1 minute, for example) to be added to the initial lighting time t0 each time the section t4 has elapsed. As an example, assuming that the predetermined value is 1 minute, a factor (N times) by which the t4 should be multiplied for obtaining the t2 is calculated, first, and then, a result obtained by adding N minutes to t0 may be used as the lighting time t1.

In an embodiment as described above, the control unit 200 allows the ultraviolet lamp 100 to be on for a predetermined time period by controlling the outer-door switch 201, the relay 202, and the timer 205 and using opening/closing of the outer door 3 as a trigger. Thus, the control unit 200, the outer-door switch 201, the relay 202, and the timer 205 and the ROM 206 for storing the predetermined program for allowing the control unit 200 to execute such processing, correspond to a lighting device.

Also, in an embodiment as described above, the control unit 200 acquires the accumulated lighting time period of the ultraviolet lamp 100 by controlling the timer 205 and the RAM 207, and detects an increase of the accumulated lighting time period by the unit of 200 hours, for example, as a degree of deterioration in the disinfection capability of the ultraviolet lamp 100. Thus, the control unit 200, the timer 205, and the RAM 207 and the ROM 206 for storing the predetermined program for allowing the control unit 200 to execute such processing, correspond to a detecting device.

Moreover, in an embodiment as described above, the control unit 200 acquires the lighting time t1 corresponding to the accumulated lighting time t2 (Step S105 in FIG. 4) on the basis of the table data stored in the RAM 207. Thus, the control unit 200 and the timer 205, and the ROM 206 for storing the predetermined program for allowing the control unit 200 execute such processing, correspond to a controller.

Other Embodiments

The above embodiments of the present invention are simply for facilitating the understanding of the present invention and are not in any way to be construed as limiting the present invention. The present invention may variously be changed or altered without departing from its spirit and encompass equivalents thereof.

In an embodiment as described above, detection of deterioration of the disinfection capability of the ultraviolet lamp 100 is performed by the control unit 200, the timer 205, the ROM 206 for storing the predetermined program, and the RAM 207, however, this is not limitative.

For example, a predetermined ultraviolet sensor (not shown) is provided in the culture chamber 4*b* to detect intensity of the ultraviolet ray applied from the ultraviolet lamp 100, and based on such a detection result of the ultraviolet sensor, the control unit 200 may set the predetermined time period, during which the ultraviolet lamp 100 is on, longer as the intensity of the ultraviolet ray becomes weaker. As a result, the deteriorated portion of the disinfection capability caused by drop in the intensity of the ultraviolet ray is compensated for by an extension of the predetermined time period during which the ultraviolet lamp 100 is on, and thus, the deterioration in the disinfection effect of the ultraviolet lamp 100 when the culture chamber 4*b* is sealed can be suppressed.

Also, for example, there is provided a predetermined current measuring means (not shown) for measuring a discharge current in the ultraviolet lamp 100, and the deterioration in the disinfection capability of the ultraviolet lamp 100 may be detected on the basis of the degree of drop in a current value measured by the current measuring means.

Moreover, for example, there is provided a predetermined counter (not shown) for measuring the number of times the outer door 3 is changed from the open state to the closed state, and a measured value by this counter may be used instead of the above-mentioned accumulated lighting time period. If such a situation hardly occurs that the outer door 3 is opened while the ultraviolet lamp 100 is on and the lighting is interrupted (Steps S112 to S115 in FIG. 4), a measured value by the counter is substantially in proportion to the accumulated lighting time period.

Also, in an embodiment described as above, sealing of the culture chamber 4*b* in the culture apparatus 1 is detected through an operation of closing the outer door 3 with the outer-door switch 201, however, this is not limitative, it may be detected by an operation of closing the inner door 4*a*, for example. In this case, it is only required to provide a micro switch, for example, which detects the closing operation of the inner door 4*a*. However, if opening/closing of the inner door 4*a* is interlocked with lighting on/off of the ultraviolet lamp 100, the inner door 4*a* needs to be formed by a material absorbing an ultraviolet ray or the like for safety reasons.

Also, in an embodiment as described above, the ultraviolet lamp 100 is disposed so as to be located at the lower part of the duct 43 and above the humidification tray 44 (See FIGS. 1 and 2), but this is not limitative. The ultraviolet lamp 100 may be disposed at any position as long as bacteria can effectively be disinfected in the air and water for humidification in the humidification tray 44 in the culture chamber 4*b*, and is located at a position at which the culture is not adversely affected, for example.

Also, in an embodiment as described above, a section of the accumulated lighting time period used for extending the lighting time period of the ultraviolet lamp 100 at each lighting is a fixed value such as 200 hours (See FIG. 5), however, this is not limitative, and it may be such a variable value (this is also a predetermined time period) as to be reduced gradually each time, etc., for example.

Also, in an embodiment as described above, there is described the case in which the disinfection capability of the ultraviolet lamp 100 is deteriorated with a linear relationship with the accumulated lighting time period (See FIG. 5), but this is not limited to that. The culture apparatus 1 can be also applied to a case in which the disinfection capability of the ultraviolet lamp 100 is deteriorated with a non-linear relationship in which an absolute value of a deterioration gradient is gradually increased with respect to the accumulated lighting time period, for example. In this case, it is only required to extend the lighting time period of the ultraviolet lamp 100 at each lighting according to a known relationship between the accumulated lighting time period and the deterioration in the disinfection capability.

Also, in an embodiment as described above, the lighting time period of the ultraviolet lamp 100 at each lighting is set according to the deterioration in the disinfection capability of the ultraviolet lamp 100, however, this is not limitative, and a frequency of an AC voltage to be applied to the ultraviolet lamp 100 may be set or the voltage may be set, for example.

Also, in an embodiment as described above, the ultraviolet lamp 100 is used, but a means for generating an ultraviolet ray may be LED (Light-Emitting Diode) or the like.

<Culture Apparatus>

Figure 6:
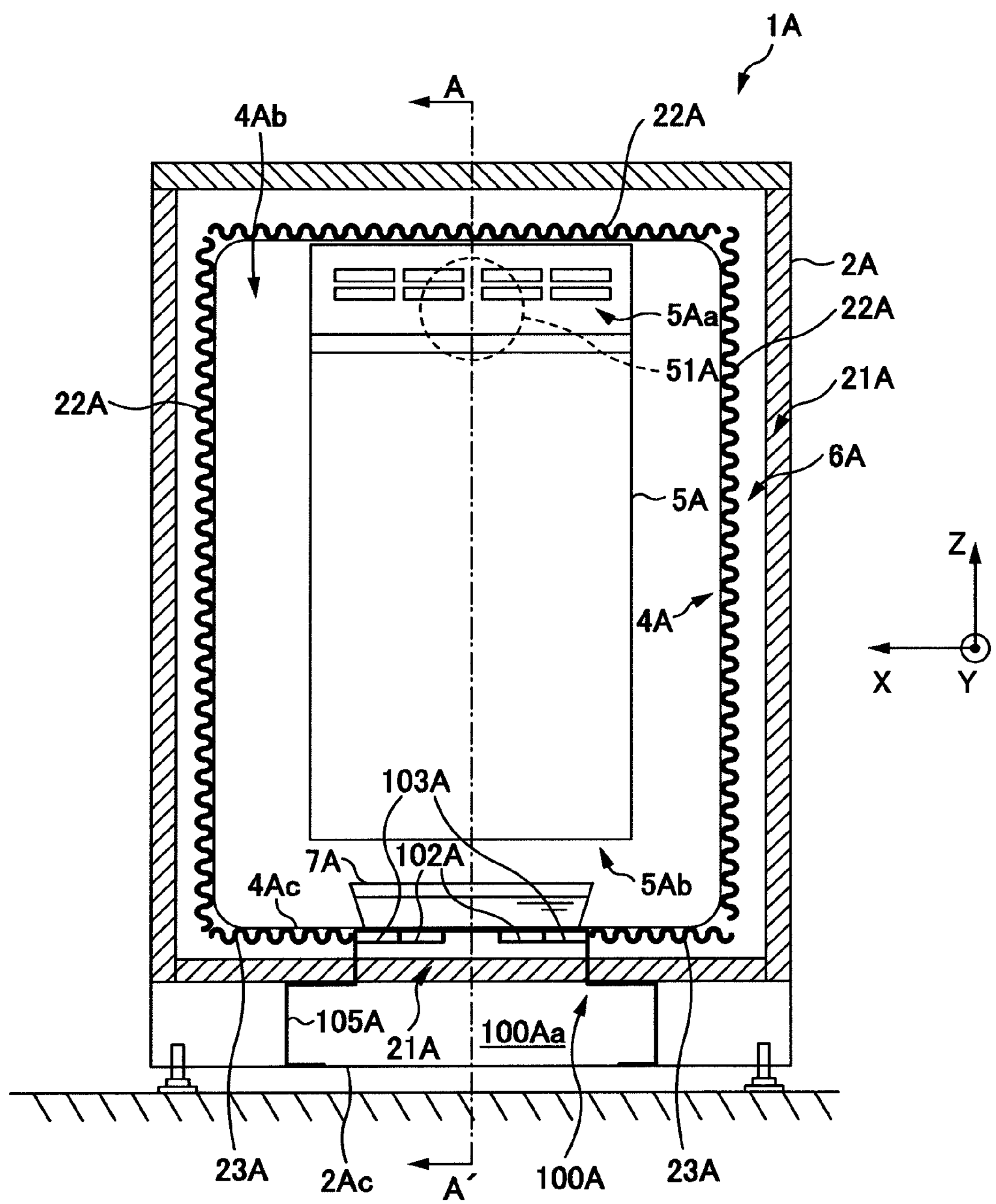
FIG. 6 is a front sectional view of an example of a culture apparatus according to a second embodiment.

FIG. 6 is a front sectional view of an example of a culture apparatus 1A according to an embodiment illustrating an arrangement of a heater.

The culture apparatus 1A includes an insulation housing including an inner box 4A, an outer box 2A, heaters 22A and 23A (first heater), an insulating material 21A (first insulating material), and an opening on a front side (+Y side), an outer door (insulation door) 3A, and a radiation member 100A.

The heaters 22A and 23A are disposed outside the inner box 4A and heat the inside of a culture chamber 4Ab. Here, the heater 22A is disposed on each outside of a side plate (±X side plate), a back plate (−Y side plate), and a top plate (+Z side plate) of the inner box 4A. Also, the heater 23A is disposed around the radiation member 100A, which will be described later, on the outside a bottom plate 4Ac (−Z side plate) of the inner box 4A, and heats the inside of the culture chamber 4Ab as well as heats water in a humidification tray (water storage tray) 7A.

The insulating material 21A is disposed inside the outer box 2A and keeps the temperature of the inside of the insulation material 21A. An air jacket 6A as a circulation path for air, for example, is formed between the insulating material 21A and the inner box 4A to further keep the temperature of the inner box 4A, and the above-mentioned heaters 22A and 23A are disposed in this air jacket 6A.

The culture apparatus according to an embodiment of the present invention can also be employed for the culture apparatus according to a first embodiment.

What is claimed is:

1. A culture apparatus comprising:

a housing including a culture chamber inside, culture being cultured in the culture chamber;

a door configured to seal the culture chamber;

an ultraviolet lamp configured to generate an ultraviolet ray for disinfecting air in the culture chamber;

a lighting device configured to allow the ultraviolet lamp to be on for a predetermined time period, when the air in the culture chamber is disinfected;

a detecting device configured to detect deterioration of disinfection capability of the ultraviolet lamp; and a controller configured to correct the predetermined time period, during which the ultraviolet lamp is on, so as to be longer according to the deterioration of the disinfection capability of the ultraviolet lamp detected by the detecting device, wherein the detecting device outputs as the detection result an accumulated time period obtained by accumulating a lighting time period of the ultraviolet lamp, the controller controls the lighting device so that the predetermined time period is set longer as the accumulated time period becomes longer, and the controller controls the lighting device so that the predetermined time period is set longer in a stepwise manner each time the accumulated time period reaches a predetermined time period.

2. The culture apparatus according to claim 1, wherein the ultraviolet ray has a wavelength at which generation of ozone is suppressed.

3. The culture apparatus according to claim 1, further comprising a switch configured to detect whether the door is open or closed, wherein lighting of the ultraviolet lamp is started when closing of the door is detected by the switch.

* * * * *